United States Patent [19]
Weaver

[11] Patent Number: 5,693,052
[45] Date of Patent: Dec. 2, 1997

[54] COATED BIPOLAR ELECTROCAUTERY

[75] Inventor: Drew D. Weaver, Sandy, Utah

[73] Assignee: MegaDyne Medical Products, Inc., Draper, Utah

[21] Appl. No.: 523,087

[22] Filed: Sep. 1, 1995

[51] Int. Cl.⁶ ..................... A61B 17/39
[52] U.S. Cl. ..................... 606/51; 606/50
[58] Field of Search ............. 606/45, 48, 49, 606/50, 51, 52

[56] References Cited

U.S. PATENT DOCUMENTS

| | | | |
|---|---|---|---|
| Re. 29,088 | 12/1976 | Shaw | 606/29 |
| 3,685,518 | 8/1972 | Beverle et al. | 606/51 |
| 3,902,494 | 9/1975 | Haberlen et al. | 606/49 |
| 4,074,718 | 2/1978 | Morrison, Jr. | |
| 4,427,006 | 1/1984 | Nottke | |
| 4,785,807 | 11/1988 | Blanch | |
| 4,936,842 | 6/1990 | D'Amelio | |
| 5,196,009 | 3/1993 | Kirwan, Jr. | |

FOREIGN PATENT DOCUMENTS 3447156   7/1986   Germany ................. 606/51

*Primary Examiner*—Lee S. Cohen
*Attorney, Agent, or Firm*—John L. Sigalos

[57] ABSTRACT

As electrosurgical instrument that has characteristics especially attractive in performing bipolar electrosurgery. It is believed that the relatively high current densities typically employed in using bipolar instruments result in very high incidents of sticking and other undesired characteristics when such instruments are coated with conventional coatings. A nickel-free high chromium content composite coating that manifests undesired characteristics when employed with monopolar electrosurgical implements has unexpectedly been discovered to embody very desirable characteristics when employed with bipolar instruments and is therefore efficaciously employed as a coating on bipolar implements.

4 Claims, 1 Drawing Sheet

COATED BIPOLAR ELECTROCAUTERY

BACKGROUND OF THE INVENTION

This invention relates to coated bipolar electrosurgical instruments and more particularly to such instruments that are adapted for electrosurgery at relatively high electrical current densities.

As is known to those skilled in the art, modern surgical techniques typically employ radio frequency cautery to stanch bleeding encountered in performing surgical procedures. For historical perspective and details of such techniques, reference is made to U.S. Pat. No. 5,196,009. As mentioned therein, typical problems encountered while conducting electrosurgery include charting of cauterized tissue and sticking of tissue to surfaces of surgical implements. This patent tries to overcome such problem by making the first and second blade portions entirely of nickel. This is not only costly, but still does not satisfactorily prevent sticking of charred blood and tissue. Further, nickel is bio-reactive and, thus, not desired for use in contact with tissue.

Charring and sticking problems have been greatly ameliorated through discovery that certain coatings have particularly attractive characteristics. For example, Teflon coatings of certain thicknesses when used with monopolar electrosurgical instruments have been found to greatly reduce sticking of charred tissue while still preserving attractive electrical characteristics. An example of such is the coating described and claimed in U.S. Pat. No. 4,785,807. However, when such coatings have been employed in bipolar procedures, their advantages have either disappeared or become greatly ameliorated; and, thus, there has continued to be a need for an improved coating that is advantageously effective when used in bipolar electrosurgery.

BRIEF SUMMARY OF THE INVENTION

The improved surgical implement according to the invention hereof includes a bipolar electrosurgical instrument the surgical stainless steel working surfaces of which are covered with a thin coating of a metal having at least about twice the thermal conductivity of surgical stainless steel. Preferably, the thickness of the coating is in a range of thickness of about 0.0001 to about 0.0005 inches. The exact composition of the coating material may vary. However, the preferred coating material is a nickel-free high chromium composite sold under the designation ME-92 by Electrolizing Inc., 10 Houghton Street, Providence, R.I. 02904, U.S.A. It is a highly precise, non-magnetic, medically safe, USP Class VI Tripartite/ISO (International Standards Organization) certified nickel-free high chromium-composite providing a surface coating having a hardness Rc80 for stainless steels. It features a very smooth, fine molecular-grained, non-porous coating. It also has been found to transfer radio frequency electrical energy efficiently and effectively at the relatively high current densities encountered when employing bipolar surgical techniques without any destruction of the composite coating.

OBJECTS AND FEATURES OF THE INVENTION

It is one general object of the invention to improve bipolar electrosurgical instruments.

It is yet another object of the invention to coat bipolar electrosurgical instruments with a non-sticking and relatively high current density coating.

Accordingly, in accordance with a feature of the invention, a metal having a thermal conductivity at least about twice that of surgical steel, preferably a chromium-rich composite material, is applied to the exterior working surfaces of electrosurgical instruments, thereby improving non-sticking characteristics while permitting use of relatively high cauterizing current densities.

These and other objects and features of the invention will be apparent from the following description, byway of example of a preferred embodiment, with reference to the drawing.

DESCRIPTION OF A PREFERRED EMBODIMENT

Figure 1:
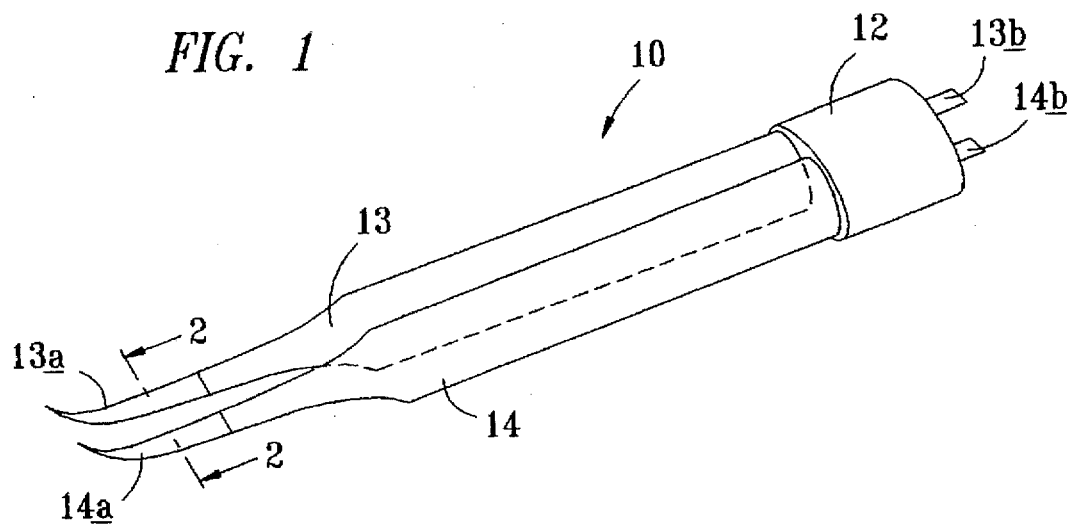
FIG. 1 is a perspective view of a bipolar electrosurgical instrument having an improved coating in accordance with the invention hereof.

Now turning to the drawing, and more particularly FIG. 1 thereof, it will be seen to illustrate a bipolar electrosurgical instrument according to this invention. There it will be observed is instrument 10 having an electrode holding portion 12 from which there extend electrodes 13 and 14 having coatings 13a and 14a of the preferred nickel-free chromium thereon. It is conventional to have bipolar electrodes in the shape of forceps, blades, needles, paddles, waffles, and the like. In holding portion 12 there typically are provided conventional electrical connections to a source of radio frequency energy (not shown).

Figure 2:
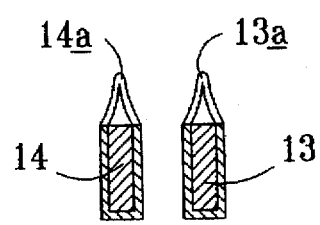
FIG. 2 is a section view taken along the section lines 2—2 of FIG. 1 and showing the improved coatings in greater detail.

In FIG. 2 are seen electrodes 13 and 14 which are coated on their working surfaces with the aforementioned relatively thin coatings 13a and 14a of the composite material as described above. The thicknesses of such coatings preferably are in the range of 0.0001 to 0.0005 inches but are exaggerated as shown in order to be clearly observable in the drawing. As used herein, the term "working" surfaces mean not only those portions of electrodes 13 and 14 that comes in contact with patient tissue, but also portions extending backwardly to electrode holding portion 12 not intended to contact tissue. The extended coverage is to ensure rapid conduction of heat from the tissue contact points of electrodes 13 and 14 to dissipate that heat in the stainless steel portion of such electrodes. This helps ensure non-sticking.

Other metal coatings that can be used are gold, silver, aluminum, and like metals which are not toxic to tissue and which have a thermal conductivity at least about twice that of surgical stainless steel.

In electrode holding portion 12 there is conventional insulating material (not shown) which holds electrodes 13 and 14 in position and provides the needed electrical insulating therebetween. Proximal ends 13b and 14b of the electrodes extend so as to facilitate conventional connections thereto of electrical conductors conveying the aforementioned radio frequency electrical energy.

As mentioned above, the high chromium-composite coating according to the invention was found to be ineffective when used to coat conventional monopolar electrosurgical implements. However, contrary to expectations, the coating was unexpectedly found to exhibit unusually attractive non-stick attributes when utilized with bipolar instruments. The reasons for this are not completely understood. It is known that the stainless steel electrodes of bipolar electrodes are much larger in size than monopolar electrodes, some 20 to 40 times larger, and that heat transfer is area dependent, the larger the area to which heat can be conducted the more heat can be transferred away from the electrocautery site to other areas of the electrode. It is theorized that the instant coatings, because they cover a larger area than that possible on monopolar electrodes and because of their much higher thermal conductivity, rapidly transfer heat away from the cautery site to the stainless steel substrates (much larger than that of monopolar electrodes) which act as much greater capacity heat sinks, thereby minimizing heat buildup as the cautery site and minimizing sticking of debris to the electrodes.

As a consequence, by coating with chromium so as to rapidly conduct heat from the contact point along the chromium coating to the major stainless steel portion of the bipolar electrodes, the heat generated by cauterization can be rapidly dissipated enabling cauterization without sticking.

Although the invention hereof has been described byway of a preferred embodiment, it will be evident that adaptations and modifications may be employed without departing from the spirit and scope thereof.

The terms and expressions employed herein have been used as terms of description and not of limitation; and, thus, there is no intent of excluding equivalents, but on the contrary it is intended to cover any and all equivalents that may be employed without departing from the spirit and scope of the invention.

What is claimed is:

1. A bipolar electrocautery implement comprising:
    (a) a surgical instrument having
        (i) a first electrode with a first working surface, said first electrode being adapted for interconnection with a first of two electrical terminals from a radio frequency electrocautery voltage source; and
        (ii) a second electrode with a second working surface, said second electrode being adapted for interconnection with a second of two electrical terminals from a radio frequency electrocautery voltage source; and
    (b) coating means for transferring radio frequency energy therethrough to effect cautery, said coating means being disposed on at least portions of said first and said second working surfaces meant to contact tissue, and wherein said coating means consists of a nickel-free high chromium composite having a thermal conductivity at least about twice that of surgical stainless steel.

2. The bipolar electrocautery implement according to claim 1 wherein said coating means is effective to transfer said energy therethrough at current densities ranging from 0.0001 to 10.0 amperes per square centimeter.

3. A bipolar electrocautery implement according to claim 1 wherein said coating means essentially covers said first and said second working surfaces.

4. A bipolar electrocautery implement according to claim 1 wherein thickness of said coating means lies within a range of from about 0.0001 to about 0.0005 inch.

* * * * *